United States Patent
Davis et al.

(10) Patent No.: US 10,398,318 B2
(45) Date of Patent: *Sep. 3, 2019

(54) CANNULA WITH PROXIMALLY MOUNTED CAMERA

(71) Applicant: Rebound Therapeutics Corporation, Irvine, CA (US)

(72) Inventors: Peter G. Davis, Irvine, CA (US); Ross Tsukashima, Irvine, CA (US); Jeffrey J. Valko, Irvine, CA (US); Michael R. Henson, Irvine, CA (US); Todd D. McIntyre, Irvine, CA (US)

(73) Assignee: Rebound Therapeutics Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/240,690

(22) Filed: Jan. 4, 2019

(65) Prior Publication Data

US 2019/0133459 A1 May 9, 2019

Related U.S. Application Data

(63) Continuation of application No. 15/239,632, filed on Aug. 17, 2016, now Pat. No. 10,172,525.

(Continued)

(51) Int. Cl.
*A61B 1/00* (2006.01)
*A61B 5/02* (2006.01)
(Continued)

(52) U.S. Cl.
CPC ...... *A61B 5/02007* (2013.01); *A61B 1/00087* (2013.01); *A61B 1/00135* (2013.01);
(Continued)

(58) Field of Classification Search
CPC . A61B 5/02007; A61B 5/1473; A61B 5/6848; A61B 5/6868; A61B 1/00087;
(Continued)

(56) References Cited

U.S. PATENT DOCUMENTS

| 5,004,332 A | 4/1991 | Edwards |
| 5,957,832 A | 9/1999 | Taylor et al. |

(Continued)

FOREIGN PATENT DOCUMENTS

| EP | 2430992 | 3/2012 |
| JP | 201616053 | 2/2016 |

(Continued)

OTHER PUBLICATIONS

Examination Report dated Mar. 12, 2019 from Australian Patent Application No. 2018201138.

(Continued)

*Primary Examiner* — Timothy J Neal
(74) *Attorney, Agent, or Firm* — K. David Crockett, Esq.; Crockett & Crockett, PC

(57) ABSTRACT

A cannula with a proximally mounted camera provides visualization of the brain during minimally invasive surgery. The device comprises a cannula with a camera mounted on the proximal end of the cannula with a view into the cannula lumen and the surgical field below the lumen. A prism, reflector or other suitable optical element is oriented between the camera and the lumen of the cannula to afford the camera a view into the cannula while minimizing obstruction of the lumen.

11 Claims, 4 Drawing Sheets

Related U.S. Application Data

(60) Provisional application No. 62/206,115, filed on Aug. 17, 2015.

(51) Int. Cl.

| | | |
|---|---|---|
| *A61B 1/313* | (2006.01) | |
| *A61B 1/05* | (2006.01) | |
| *A61B 17/34* | (2006.01) | |
| *A61B 1/06* | (2006.01) | |
| *A61B 5/145* | (2006.01) | |
| *A61B 5/1473* | (2006.01) | |
| *A61B 5/00* | (2006.01) | |
| *A61B 90/00* | (2016.01) | |
| *A61B 90/30* | (2016.01) | |

(52) U.S. Cl.
CPC .......... *A61B 1/00188* (2013.01); *A61B 1/053* (2013.01); *A61B 1/06* (2013.01); *A61B 1/313* (2013.01); *A61B 5/1473* (2013.01); *A61B 5/14532* (2013.01); *A61B 5/6848* (2013.01); *A61B 5/6868* (2013.01); *A61B 5/6886* (2013.01); *A61B 5/742* (2013.01); *A61B 17/3421* (2013.01); *A61B 2090/309* (2016.02); *A61B 2090/3614* (2016.02)

(58) Field of Classification Search
CPC ....... A61B 1/06; A61B 1/00135; A61B 1/053; A61B 1/00188; A61B 1/313; A61B 17/3421; A61B 2090/3614
See application file for complete search history.

(56) References Cited

U.S. PATENT DOCUMENTS

| | | | |
|---|---|---|---|
| 6,361,488 B1 | 3/2002 | Davison | |
| 9,216,015 B2 | 12/2015 | Wilson | |
| 10,105,042 B2 * | 10/2018 | Davis .................. | A61B 1/07 |
| 2002/0022764 A1 | 2/2002 | Smith et al. | |
| 2004/0102804 A1 | 5/2004 | Chin | |
| 2005/0191046 A1 | 9/2005 | Dehmel et al. | |
| 2006/0069314 A1 | 3/2006 | Farr | |
| 2008/0058594 A1 | 3/2008 | Xie | |
| 2008/0109026 A1 | 5/2008 | Kassam | |
| 2009/0048622 A1 | 2/2009 | Wilson | |
| 2009/0318758 A1 | 12/2009 | Farr | |
| 2010/0013910 A1 | 1/2010 | Farr | |
| 2010/0081988 A1 | 4/2010 | Kahle et al. | |
| 2011/0087159 A1 | 4/2011 | Parihar et al. | |
| 2011/0160535 A1 | 6/2011 | Bayer et al. | |
| 2011/0251456 A1 | 10/2011 | Jacobsen et al. | |
| 2012/0224263 A1 | 9/2012 | Gallagher | |
| 2014/0275771 A1 | 9/2014 | Henley | |
| 2014/0324080 A1 | 10/2014 | Wallace | |
| 2015/0265369 A1 | 9/2015 | Garbey et al. | |
| 2015/0366583 A1 | 12/2015 | Druma et al. | |
| 2016/0045224 A1 | 2/2016 | Hendershot, III | |

FOREIGN PATENT DOCUMENTS

| | | |
|---|---|---|
| WO | WO2001054560 | 8/2001 |
| WO | WO2009094644 | 7/2009 |
| WO | WO2013092222 | 6/2013 |
| WO | WO2015135057 | 9/2015 |

OTHER PUBLICATIONS

Examination Report dated Oct. 25, 2017 from Australian Patent Application No. 2017232046.
Combined Search and Examination Report dated Sep. 28, 2017 from Great Britain Patent Application No. 1714253.0.
Combined Search and Examination Report dated Sep. 28, 2017 from Great Britain Patent Application No. 1714722.4.
International Search Report and Written Opinion dated Jan. 15, 2018 from International Application No. PCT/US2017/047424.
Office Action dated Jul. 17, 2018 from U.S. Appl. No. 15/895,277.
Office Action dated Jul. 17, 2018 from U.S. Appl. No. 15/895,335.
Office Action from U.S. Appl. No. 16/168,662 dated May 22, 2019.

* cited by examiner

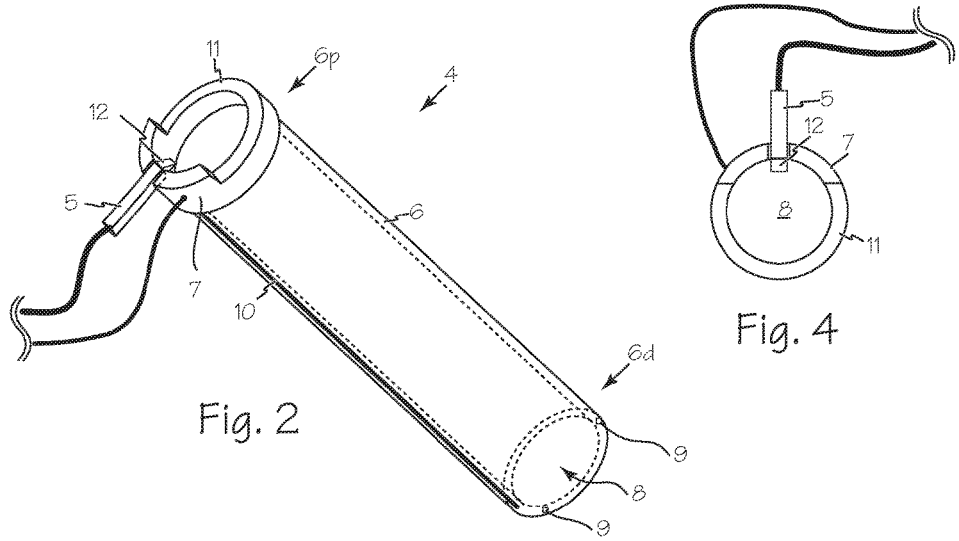
Fig. 2
Fig. 4
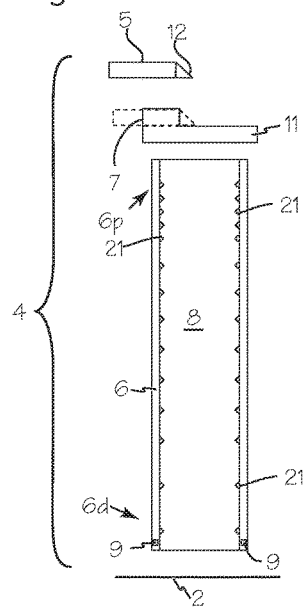
Fig. 3
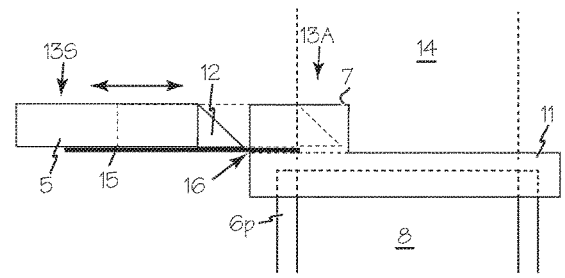
Fig. 5
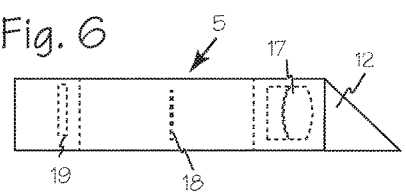
Fig. 6

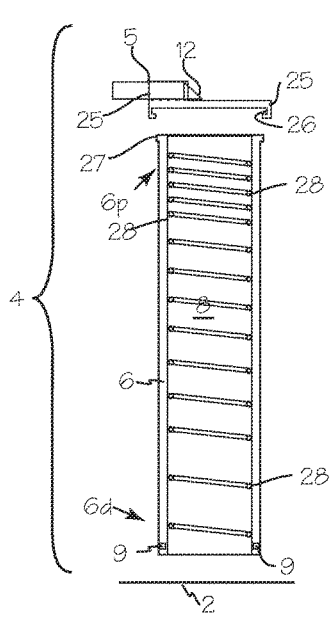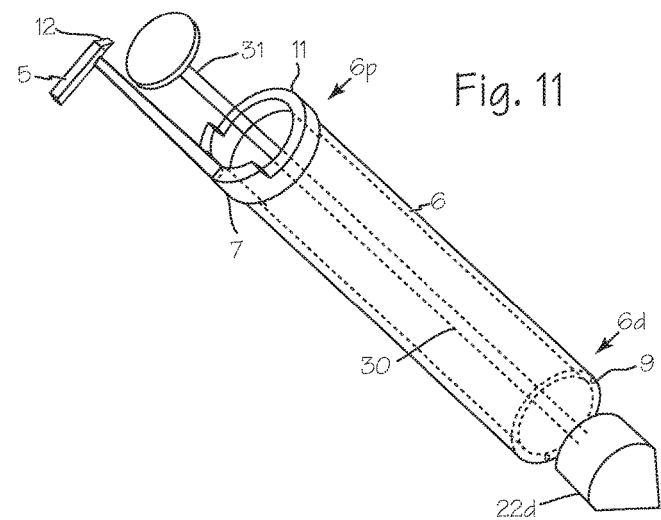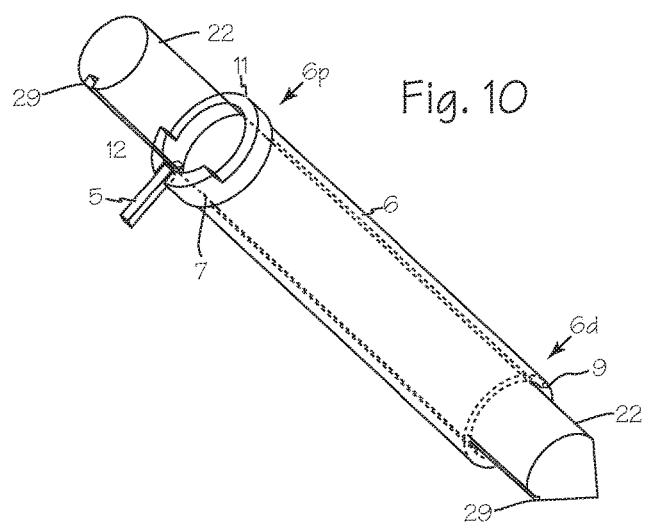

CANNULA WITH PROXIMALLY MOUNTED CAMERA

This application is a continuation of U.S. application Ser. No. 15/239,632, filed Aug. 17, 2016, now U.S. patent Ser. No. 10/172,525, which claims priority to U.S. Provisional Patent Application 62/206,115 filed Aug. 17, 2015.

FIELD OF THE INVENTIONS

The inventions described below relate to the field of minimally invasive brain surgery.

BACKGROUND OF THE INVENTIONS

Stroke is a common cause of death and disabling neurologic disorder. Approximately 700,000 patients suffer from stroke in the United States every year. Hemorrhagic stroke accounts for 20% of the annual stroke population. Hemorrhagic stroke is due to a rupture of a blood vessel in the brain, causing bleeding into the brain tissue and resulting in a hematoma (a blood mass) in the brain. Prompt removal of the blood mass is necessary to limit or prevent long-term brain injury. Clear visualization and imaging of the blood mass and any surrounding surgical field facilitates removal of the blood mass.

SUMMARY

The devices and methods described below provide for improved visualization of the brain during minimally invasive surgery. The device comprises a cannula with a camera mounted on the proximal end of the cannula with a view into the cannula lumen and the tissue within and below the lumen. A prism, reflector or other suitable optical element is oriented between the camera and the lumen of the cannula to afford the camera a view into the cannula while minimizing obstruction of the lumen.

BRIEF DESCRIPTION OF THE DRAWINGS

FIG. 2 illustrates a cannula with a proximally mounted camera.

FIG. 3 is an exploded side view of a cannula with a proximally mounted camera.

FIG. 4 is a top view of a cannula with a proximally mounted camera.

FIG. 5 is a close-up side view of a cannula light shield with the camera movable on a track.

FIG. 6 is a close-up side view of the camera for a cannula with a proximally mounted camera.

FIG. 9 illustrates an additional structure of the cannula which provides for easy attachment and detachment of the camera to the cannula tube.

FIGS. 10 and 11 illustrate the camera and cannula system in which the camera is fixed to the cannula tube, and the obturator is modified to pass the camera even as it encroaches on the space over the lumen of the cannula tube.

DETAILED DESCRIPTION OF THE INVENTIONS

Figure 1:
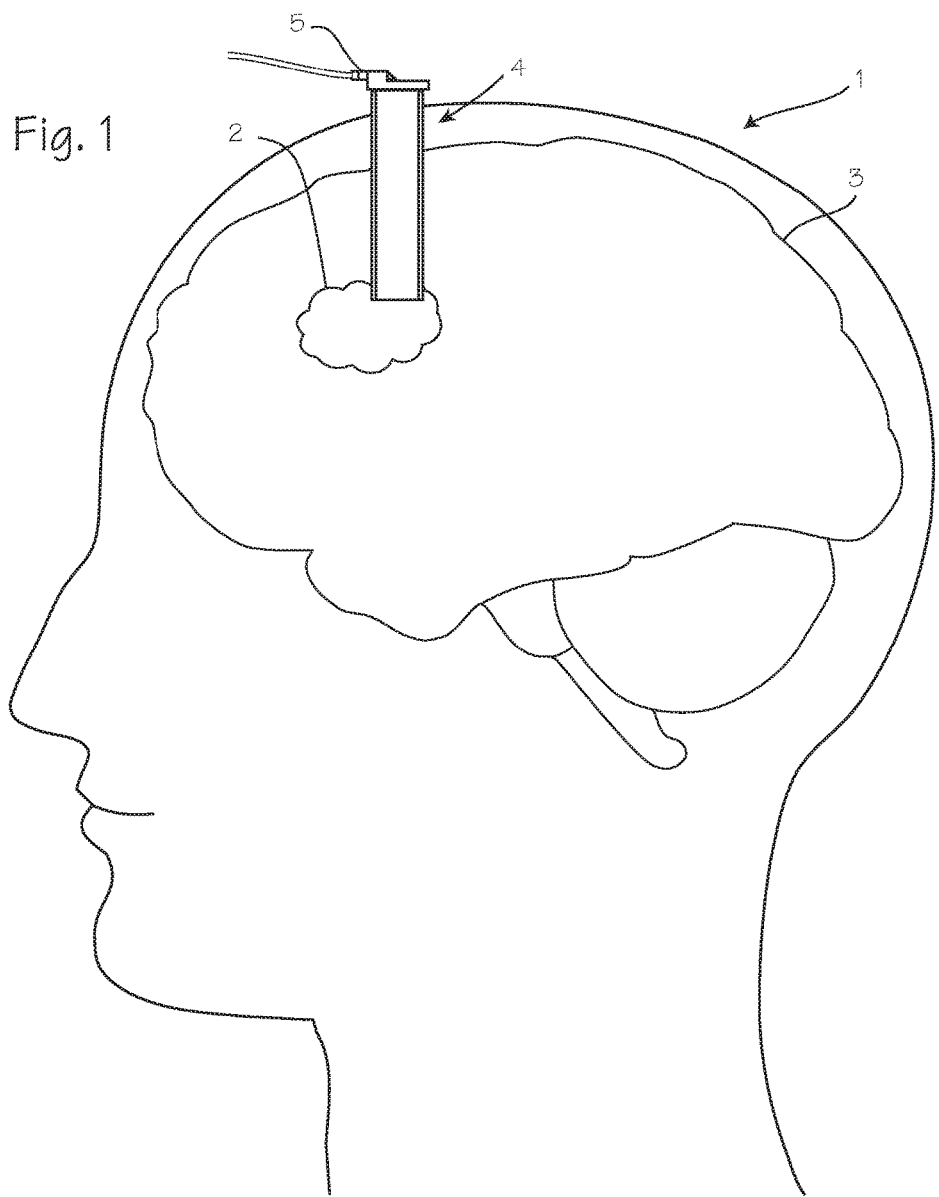
FIG. 1 illustrates the head of a patient with an area requiring surgical intervention.

FIG. 1 illustrates a patient 1 with a blood mass 2 in the brain 3 that necessitates surgical intervention. A cannula 4 has been inserted into the brain, with the distal end of the cannula proximate the blood mass. A camera 5 is mounted on the proximal rim of the cannula, with a portion of the camera overhanging the rim of the cannula and disposed over the lumen of the cannula, and is operable to obtain video or still images of the blood mass or other tissue at the distal end of the cannula.

FIG. 2 illustrates the cannula 4 in detail. The cannula comprises a cannula tube 6 with a camera 5 and one or more light sources and a mounting structure 7 secured to the proximal end of the cannula. The camera, shown in more detail in the following figures, includes a prism, a reflector or other mirror structure or optical element, overhanging the lumen 8 of the cannula tube. The light necessary to provide good visualization of the blood mass, and obtain images of the blood mass, may be provided by LED's 9 (or other light source) disposed at the distal end 6d of the cannula tube, at or proximate the distal opening. The LED's may instead be disposed at the proximal end of the cannula tube and the light may be transmitted through optical fibers 10, or, if the cannula is made of a transparent material, the light may be transmitted down the walls of the cannula tube to exit the distal end of the cannula wall to illuminate the blood mass. The ring 11 of the mounting structure 7 serves as a shield to block light from view from a proximal viewpoint, whether the light emanates directly from proximally located lights, or passes through the cannula tube from distally located lights. In embodiments in which the light sources are disposed on the proximal and of the cannula tube, the distal portion 6d of the cannula tube may shaped, molded, machined, treated or otherwise configured to enable the emergence of light from cannula tube 6 to illuminate the surgical field. For example, inner distal surface and or outer distal surface may be sanded or frosted to enable emission of light through the surfaces. Cables for providing power to the camera and light source, and carrying image data from the camera to a display, may be provided, or the device may be powered by batteries disposed on the device and image data can be transmitted wirelessly to a display.

FIG. 3 is an exploded side view of cannula 4 with the camera 5 disposed on the proximal rim of the cannula tube, with a prism 12 overhanging the lumen 8 of the cannula. FIG. 4 illustrates a top view of cannula 4 with a proximally mounted camera 5. FIG. 3 also shows the LEDs 9 disposed on or near the distal end 6P of the cannula tube to emit light into the surgical field (such as blood mass 2).

Preferably, the camera is mounted within the mounting structure so that the prism may be removed from its overhanging position, either by sliding the camera radially, flipping the camera around a pivot, or by removing the camera from the camera mount entirely. FIG. 5 illustrates a sliding attachment of camera 5 to the mounting structure 7 as well as movement of the camera from standby position 13S to use position 13A. With camera 5 in use position 13A, prism 12 extends partially or fully into the cylindrical space 14 defined by and extending from the lumen 8 and affords an unobstructed view of surgical site at the distal opening of the cannula tube, while providing minimal interference to small diameter surgical instruments using lumen 8 to perform surgery (for example, an aspirator or a macerator). Any suitable technique for moveably attaching camera 5 to light shield 7 may be used. For example, the camera may be slidably attached on a track such as track 15, in which case the track 15 secures camera 5 to the light shield and enables the camera/prism assembly to move radially between standby position 13S to use position 13A and back again (that is, from a first position in which the prism extends into the lumen 8 or the cylindrical space 14 defined by the lumen of the cannula tube, to a second position in which the prism resides outside of lumen 8 or the cylindrical space 14 defined by the lumen of the cannula tube). The camera may also be attached with a pivot at 16, so that it is rotatably attached to the tube, from a first position in which the axis of the camera is perpendicular to the long axis of the cannula tube to a second position angles from the long axis so that the prism resides outside the cylindrical space 14 defined by the lumen of the cannula tube. The camera may also be releasably attached to the mounting structure (i.e., it may be readily attached and detached by hand, without the use of tools, during a surgical procedure) with a friction fit or detent arrangement between the camera and a channel of the mounting structure.

FIG. 6 is a close-up side view of the camera 5. The camera 5 comprises the prism 12, a lens or lenses 17 (which may include an achromatic lens or other doublet), the imaging device 18 and the control system 19 (if provided in the camera component of the system). The lens 17 may be part of an optical assembly that includes additional optical components. The imaging device 18 may be any suitable image sensor such as a CCD sensor or CMOS sensor. The control system 19 may include a controller, data processing components and transmitters such as a controller and a transmitter to control the camera and transmit data from the camera (the data output system may be located off the device). Suitable cables or wireless transmitters may be used to connect the camera to a display system and a power supply. The imaging sensor is characterized by an imaging plane, and the prism is aligned with the imaging plane to direct light directed parallel to the imaging plane toward the imaging plane. As illustrated, the imaging plane is parallel to the long axis of the cannula tube, and the prism disposed along a line perpendicular to the imaging plane, and oriented to direct light from the surgical field at the distal end of the cannula tube onto the imaging plane.

In embodiments in which illumination is provided by lights disposed on the distal end of the cannula tube, any resultant glare and reflections from the inner wall of the cannula tube can be minimized by providing baffles on the interior wall of the tube. The baffles may comprise ridges protruding slightly into the lumen, dispersed along the length of the tube. Preferably, the ridges are more closely spaced toward the proximal end of the tube, and relatively more widely spaced toward the distal end of tube. Several such ridges are illustrated in FIG. 3, marked as item 21. The ridges may be provided in any form, and may be integral to the cannula tube 6 (for example, formed during molding) or may be glued or fused onto the inner wall of the tube, or they may comprise turns of a coil, or turns of a braid, inserted into the tube or fused into the inner wall of the tube, and the coil or braid can comprise power or data cables associated with the distally located lights or distally located cameras or sensors.

Figure 7:
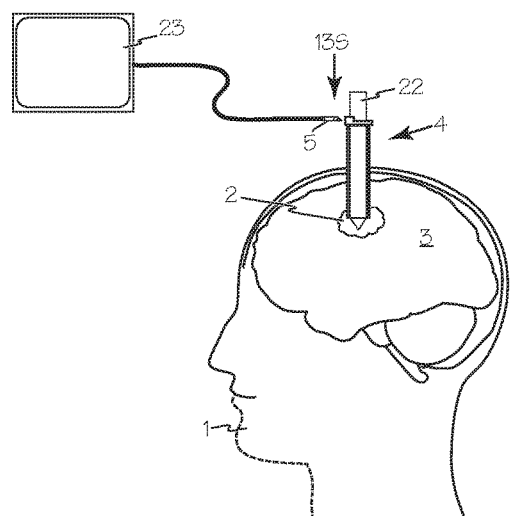
FIG. 7 illustrates the insertion of an obturator and cannula with a proximally mounted camera into a tissue mass in the patient of FIG. 1.
Figure 8:
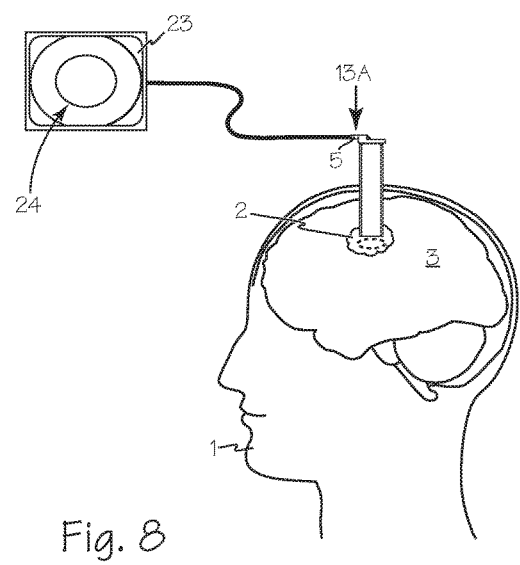
FIG. 8 illustrates the use of a cannula with a proximally mounted camera to perform minimally invasive surgery on the patient of FIG. 1.

As shown in FIGS. 7 and 8, a surgeon inserts the cannula 4 with an obturator 22 into the patient's brain until distal end 6d of the cannula is sufficiently close to tissue 2 for surgery. The surgeon then removes the obturator 22 so that the cannula 4 can be used to provide access, illumination and visibility for the surgical field. The surgeon then moves camera 5, shifting, rotating, or moving it, depending on the construction, from a standby position to place the prism over the lumen. If necessary, the surgeon orients the imaging system to obtain a view of the surgical field. With the camera in place, the surgeon operates the camera to obtain an image of the surgical field. Image data from camera 5 is transmitted to the display 23 to provide image or images 24 of the surgical field obtained through lumen 8. The image may include still images (photographs) and video. After placement of the camera, the surgeon may pass surgical instruments, or the distal end of surgical instruments, through the lumen of the cannula, while the portion of the camera is disposed within the lumen 8 or the space 14 over the lumen.

FIG. 9 illustrates an additional structure of the cannula 4 which provides for easy attachment and detachment of the camera 5 to the cannula tube 6. The camera is fixed to the mounting structure 25, and the mounting structure is releasably attachable to the cannula tube. The mounting structure comprises a ring, similar to mounting structure and ring combination shown in the previous figures (items 7 and 11) with a groove 26 on the inside of the ring, and the proximal end of the cannula tube includes a flange 27, sized and dimensioned to fit snugly in the groove of the mounting structure. The mounting structure may be snapped onto the cannula, when desired, to position the camera on the proximal end of the cannula tube, with the prism overhanging the wall of the cannula tube and disposed over the lumen 8. The mounting structure is releasably attached, in that it may be readily attached and detached by hand, without the use of tools, during a surgical procedure. Other releasable detachment means, including a friction fit between the mounting structure and the outside or inside wall of the cannula tube, or a bayonet mount, screw threads, or a magnetic attachment (with paired magnets in the cannula tube proximal end and in the mounting structure) may be used.

Also, FIG. 9 illustrates an alternative embodiment of the baffles shown in FIG. 3. In FIG. 9, the baffles comprise turns of a coil 28. The baffles may also comprise a braid. The coil or braid can also comprise the electrical wires needed to carry power to the lights disposed on the distal tip of the cannula tube, or a sensor disposed on the distal tip of the cannula tube, and can also comprise data cables needed to transmit data from any such distally mounted sensor to control or display systems associated with the sensors.

FIGS. 10 and 11 illustrate the camera and cannula system in which the camera 5 is fixed (i.e. not releasably attached) to the cannula tube 6, and the obturator 22 is modified to pass the camera even as it encroaches on the space over the lumen of the cannula tube. In FIG. 10, the obturator 22 is essentially isodiametric throughout its length, and has a groove 29 extending along its length (the portion disposed within the cannula tube). The groove is sized and dimensioned to accommodate the prism that overhangs the lumen of the cannula tube. With this construction, the obturator can be inserted into the cannula tube, and the assembled cannula and obturator can be pushed into the brain, while the cannula is in place, fixed to the cannula. In FIG. 10, the obturator 22 comprises a large diameter distal portion 22d, with an outer diameter approximately the same as the inner diameter of the cannula tube, and a small diameter rod 30 that fits easily within the lumen of the cannula tube. The camera is supported in a pylon or post 31. The post holds the camera away from the proximal opening of the cannula tube, at a sufficient distance, compared to the length of the large diameter portion 22d of the obturator, so that the obturator may be tilted or bent in order to insert large diameter portion 22d of the obturator into the lumen without the need to move the camera.

While the preferred embodiments of the devices and methods have been described in reference to the environment in which they were developed, they are merely illustrative of the principles of the inventions. The devices may be used various intracerebral procedures such as intraventricular hemorrhage procedures, neuro-stimulation procedures, and tumor resection. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

We claim:

1. A cannula system for accessing a surgical field, said cannula comprising:
   a cannula comprising a cannula tube with a proximal end and a distal end and a lumen extending from the proximal end to the distal end; and
   a camera assembly secured to the proximal end of the cannula, with a portion of the camera assembly overhanging and partially obstructing the lumen; wherein
   the camera comprises an imaging sensor and a prism, and the prism is the portion of the camera overhanging and partially obstructing the lumen; and wherein
   the prism is positioned proximally of the proximal end of the cannula tube.

2. The cannula system of claim 1 further comprising
   a mounting structure disposed on the proximal end of the cannula tube; wherein
   the camera is disposed on the mounting structure, and the camera is translatable within the mounting structure from a first position in which the camera extends into the lumen or a cylindrical space defined by the lumen of the cannula tube and extending therefrom, to a second position in which the camera resides outside of lumen or the cylindrical space defined by the lumen of the cannula tube.

3. The cannula system of claim 2 further comprising a light source disposed at the proximal end of the cannula tube, wherein the cannula tube has a distal portion having an inner surface and an outer surface and the inner surface and the outer surface are configured to enable the emergence of light from the cannula tube.

4. The cannula system of claim 1 wherein:
   the imaging sensor has an imaging plane, and the prism is aligned with the imaging plane to direct light directed parallel to the imaging plane toward the imaging plane.

5. The cannula system of claim 4 further comprising:
   a mounting structure disposed on the proximal end of the cannula tube; wherein
   the camera is disposed on the mounting structure, and the camera is translatable within the mounting structure from a first position in which the prism extends into the lumen or a cylindrical space defined by the lumen of the cannula tube and extending therefrom, to a second position in which the camera resides outside of lumen or the cylindrical space defined by the lumen of the cannula tube.

6. The cannula system of claim 1 further comprising a light source secured to the distal end of the cannula tube.

7. The cannula system of claim 6, further comprising a plurality of baffles protruding into the lumen of the cannula tube.

8. The cannula system of claim 1 further comprising a light shield operably connected to the distal end of the cannula between the one or more light sources and a user.

9. The cannula system of claim 8 wherein the imaging system is movably connected to the light shield at a pivot point.

10. The cannula system of claim 8 further comprising a track connected to the light shield wherein the imaging system is moveably engaged to the track to move laterally on the track.

11. The cannula system of claim 1 further comprising:
    a mounting structure configured for releasable attachment and detachment to the proximal end of the cannula tube; wherein
    the camera is disposed on the mounting structure such that the prism extends into a cylindrical space defined by the lumen of the cannula tube and extending therefrom when the mounting structure is attached to the proximal and of the cannula tube.

* * * * *